(12) United States Patent (10) Patent No.: US 8,830,464 B2
Feiler et al. (45) Date of Patent: Sep. 9, 2014

(54) FILM THICKNESS, REFRACTIVE INDEX, AND EXTINCTION COEFFICIENT DETERMINATION FOR FILM CURVE CREATION AND DEFECT SIZING IN REAL TIME

(71) Applicant: KLA-Tencor Corporation, Milpitas, CA (US)

(72) Inventors: David Feiler, Los Altos, CA (US); Kurt Haller, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 10 days.

(21) Appl. No.: 13/669,804

(22) Filed: Nov. 6, 2012

(65) Prior Publication Data

US 2014/0125978 A1  May 8, 2014

(51) Int. Cl.
*G01J 4/00* (2006.01)
*G01N 21/00* (2006.01)

(52) U.S. Cl.
USPC ........................................ 356/369; 356/237.5

(58) Field of Classification Search
CPC ............. G01B 11/06; G01B 11/0625; G01B 11/0641; G03F 7/70608; G03F 7/70625; G03F 7/70616; G03F 7/7065
USPC ........ 356/369, 630, 628, 243.8, 237.1–237.5, 356/335–338, 631; 250/559.19, 559.22, 250/559.27, 559.23, 559.39, 559.4–559.49
See application file for complete search history.

(56) References Cited

U.S. PATENT DOCUMENTS

| | | | |
|---|---|---|---|
| 5,728,494 A * | 3/1998 | Kawano et al. | 430/5 |
| 5,953,446 A * | 9/1999 | Opsal et al. | 382/141 |
| 6,157,444 A * | 12/2000 | Tomita et al. | 356/237.1 |
| 6,812,047 B1 * | 11/2004 | Borden et al. | 438/16 |
| 6,950,196 B2 * | 9/2005 | Fielden et al. | 356/630 |
| 7,002,675 B2 * | 2/2006 | MacGibbon et al. | 356/237.2 |
| 7,012,698 B2 * | 3/2006 | Patzwald et al. | 356/504 |
| 7,271,921 B2 | 9/2007 | Shortt | |
| 7,436,505 B2 * | 10/2008 | Belyaev et al. | 356/237.2 |
| 7,477,371 B2 * | 1/2009 | Marxer et al. | 356/237.2 |
| 7,505,619 B2 * | 3/2009 | Mapoles et al. | 382/149 |
| 7,554,656 B2 * | 6/2009 | Shortt et al. | 356/237.5 |
| 8,179,530 B2 * | 5/2012 | Levy et al. | 356/401 |
| 8,310,666 B2 * | 11/2012 | Hamamatsu et al. | 356/237.2 |
| 8,502,979 B2 * | 8/2013 | Levy et al. | 356/401 |
| 8,582,124 B2 * | 11/2013 | Yamazaki et al. | 356/630 |
| 2004/0075836 A1 * | 4/2004 | Horie et al. | 356/369 |
| 2005/0007580 A1 * | 1/2005 | MacGibbon et al. | 356/237.2 |
| 2006/0007430 A1 * | 1/2006 | Lotz et al. | 356/128 |
| 2007/0103676 A1 * | 5/2007 | Marxer et al. | 356/237.3 |
| 2007/0229809 A1 * | 10/2007 | Belyaev et al. | 356/237.2 |
| 2010/0238433 A1 * | 9/2010 | Lange et al. | 356/237.2 |
| 2010/0271621 A1 * | 10/2010 | Levy et al. | 356/73 |
| 2011/0255080 A1 * | 10/2011 | Miyoshi et al. | 356/237.1 |
| 2013/0038883 A1 * | 2/2013 | Yamazaki et al. | 356/630 |
| 2013/0083320 A1 * | 4/2013 | Gao et al. | 356/237.5 |

* cited by examiner

*Primary Examiner* — Kara E. Geisel
*Assistant Examiner* — Violeta A Prieto
(74) *Attorney, Agent, or Firm* — Suiter Swantz pc llo

(57) ABSTRACT

The present disclosure is directed to a method for inspecting a wafer, the wafer including a film deposited on a surface of the wafer. The film may have a thickness that varies over the surface of the wafer. The method includes the step of measuring the thickness, refractive index, and extinction coefficient of the film across the surface of the wafer. With this data a film curve is created in real time. The method also includes the step of determining a size of a defect on the surface based on at least the film curve.

18 Claims, 5 Drawing Sheets

FILM THICKNESS, REFRACTIVE INDEX, AND EXTINCTION COEFFICIENT DETERMINATION FOR FILM CURVE CREATION AND DEFECT SIZING IN REAL TIME

TECHNICAL FIELD

The disclosure generally relates to the field of wafer inspection by laser light scattering, and more particularly to a system and method for film curve creation and surface thickness determination for defect sizing on a wafer.

BACKGROUND

Current systems and methods for determining defect sizes on a film layer on a wafer may include the use of high precision tools to deposit a number of polystyrene latex spheres of various known sizes onto the film layer, and then measuring their light scattering intensity response in normalized parts per million (nppm). These systems and methods may not account for varying film thickness over the surface of the wafer, or variations in film thickness from one wafer to another. In addition, it is time consuming to deposit these polystyrene latex spheres.

The existing methods for measuring the thickness of a film on a wafer may present a variety of drawbacks. For example, existing methods may only provide measurements for a few points on the wafer rather than across the entire surface of the wafer. In addition, existing methods may be time consuming, as each sample may require significant time to complete. As a result, it may be difficult to determine the thickness of the film across the entire wafer surface in an accurate and timely manner.

Therefore, there exists a need for a method and apparatus to determine the sizing of defects by measuring the film thickness of a wafer, without the aforementioned shortcomings.

SUMMARY

The present disclosure is directed to a method for inspecting a wafer, the wafer including a film deposited on a surface of the wafer. The film may have a thickness that varies across the surface of the wafer. The method includes the step of measuring the thickness of the film across the surface of the wafer. The method also includes the step of determining a refractive index and an extinction coefficient for the film across the surface of the wafer. The method also involves generating a film curve based on the thickness, refractive index, and extinction coefficient of the wafer. Defect sizing can then be determined with this film curve.

The present disclosure is also directed to a system for inspecting a wafer. The wafer includes a film having a thickness that varies over the surface. The system includes a plurality of light sources arranged to project light towards the wafer. The system also includes a plurality of detectors, each detector of the plurality of detectors configured to measure light reflected from the wafer. Each detector of the plurality of detectors may also be configured to measure the polarization of light reflected from the wafer. The system also includes a processor. The processor is communicatively coupled to the plurality of detectors and is configured for calculating a refractive index, an extinction coefficient, and a film thickness for the film across the surface of the wafer. The processor is further configured for generating a film curve based on the thickness, refractive index, and extinction coefficient of the wafer.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1:
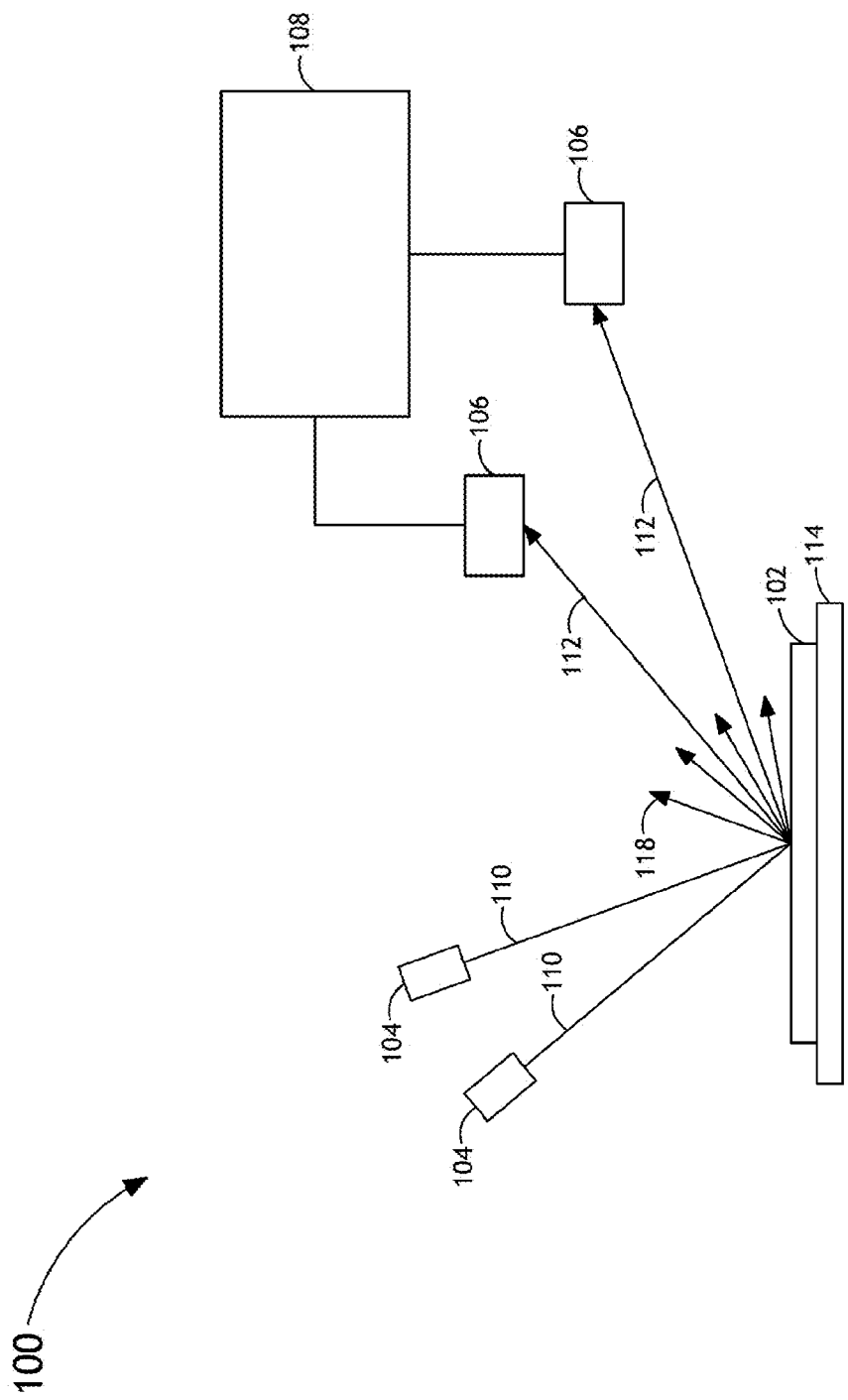
FIG. 1 is a simplified block diagram of an embodiment of a system a for inspecting a wafer.

The present disclosure is directed to a system 100 for inspecting a wafer 102 as shown in FIG. 1. The wafer 102 may include a film deposited on a surface of the wafer 102. The film may have a thickness that varies over the surface of the wafer 102. The system 100 includes a plurality of light sources 104 arranged to project light towards the wafer 102. The system 100 also includes a plurality of detectors 106. Each detector 106 of the plurality of detectors 106 may be configured to measure light reflected from the wafer 102. The detectors 106 may also be configured to measure the polarization of light reflected from the wafer 102. The system 100 also includes a processor 108. The processor 108 may be communicatively coupled to the plurality of detectors 106 and configured for calculating a refractive index, an extinction coefficient, and a film thickness for the film across the surface of the wafer 102. The processor 108 may be further configured for generating a film curve based on the thickness, refractive index, and extinction coefficient of the wafer 102.

In operation, light beams 110 travel from the light sources 104 towards the wafer 102. Some of the light from the light beams 110 may be reflected from the wafer, and some of the light may be scattered. The reflected light beams 112 may be reflected towards the detectors 106. The detectors 106 measure the polarity and intensity of the reflected light beams 112. This information is then processed by the processor 108 to determine the thickness, refractive index, and extinction coefficient of the wafer 102.

The wafer 102 of the system 100 shown in FIG. 1 may be placed on a stage 114. The stage 114 supports the wafer 102 and may rotate or move the wafer 102. The wafer 102 may be an unpatterned wafer. The wafer 102 may be a silicon wafer in one embodiment.

The film deposited on the surface of the wafer 102 may include a partially transmissive film layer or a partially reflective film layer. The film may include a single film layer, or may include a plurality of film layers of a single type or different types deposited on a surface of the wafer.

The system 100 also includes a plurality of detectors 106. The detectors 106 may be configured to measure the intensity of the light reflected from the wafer 102. The detectors 106 may also be configured to measure the polarization of light reflected from the wafer 102. The detectors 106 may include separate light intensity detectors and separate polarization detectors in one embodiment. Alternatively, each detector 106 of the plurality of detectors 106 may be configured for detecting both the polarization and the intensity of the reflected light. The detectors 106 may be configured for detecting the polarization and intensity simultaneously, or this may be completed in separate steps. The detectors 106 may also be configured for collecting other data about characteristics of the wafer 102.

The system 100 also includes a processor 108. The processor 108 may be communicatively coupled to the plurality of detectors 106 and configured for calculating a refractive index, an extinction coefficient, and a film thickness for the film across the surface of the wafer 102. The processor 108 may perform these calculations using ellipsometry in one embodiment.

The processor 108 may be further configured for generating a film curve based on the thickness, refractive index, and extinction coefficient of the wafer 102. In one embodiment, the processor 108 generates the film curve in real time to provide fast and accurate sizing of defects on the film on the surface of the wafer 102. The processor 108 may be configured to generate the film curve while the other system 100 components are determining the thickness, refractive index, and extinction coefficient of the wafer. The film curve may also change on different parts of the wafer 102 depending on the film thickness, refractive index, and extinction coefficient values for each location on the wafer 102.

The system 100 shown in FIG. 1 may be used to generate a film curve based on a film thickness, refractive index, and extinction coefficient for the wafer 102. This information may be useful for the system 100. For example, the system 100 may be used to determine the size of defects (for example, particles) on the wafer 102. The accuracy of the defect size measurements may be improved by taking into account the thickness variation over the surface of the wafer 102, as well as the refractive index, and extinction coefficient in determining the defect size. The following example describes the potential improvements in defect size measurement accuracy that may be available using the system 100 and methods described in the present disclosure.

Figure 2:
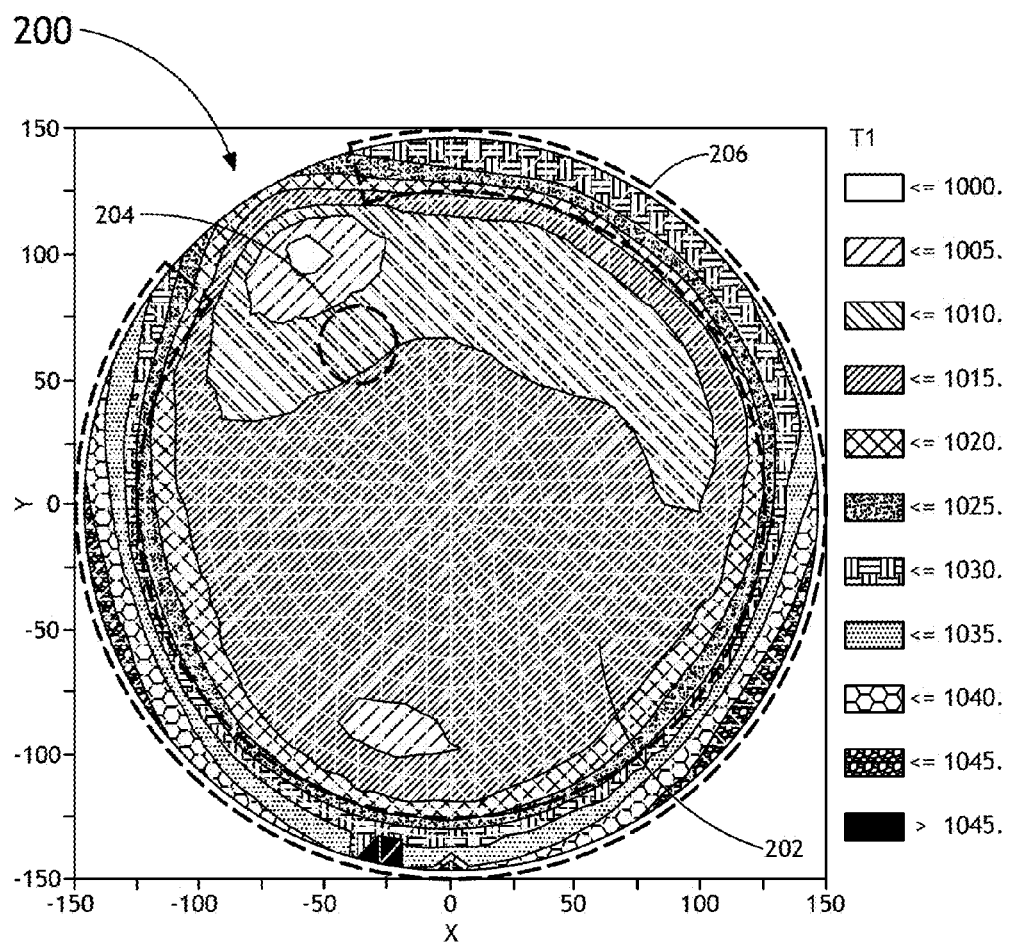
FIG. 2 shows a thickness map of an example wafer having a film deposited on a surface of the wafer, where the thickness of the film varies across the surface of the wafer.

FIG. 2 shows an example of a wafer 200 having a film 202 deposited on a surface of the wafer 200. The film 202 has a variable thickness across the surface of the wafer 200. In the example in FIG. 2, the film 202 thickness varies from about 1000 nanometers up to more than 1045 nanometers. The example will show how the variation in film 202 thickness can result in variations in particle/defect sizing over the surface of the wafer 200.

As shown in FIG. 2, a first zone 204 has an approximate film thickness of 1012 nanometers across the surface area of the first zone 204. A second zone 206 has an approximate film thickness of 1030.8 nanometers across the surface area of the second zone 206.

Figure 3:
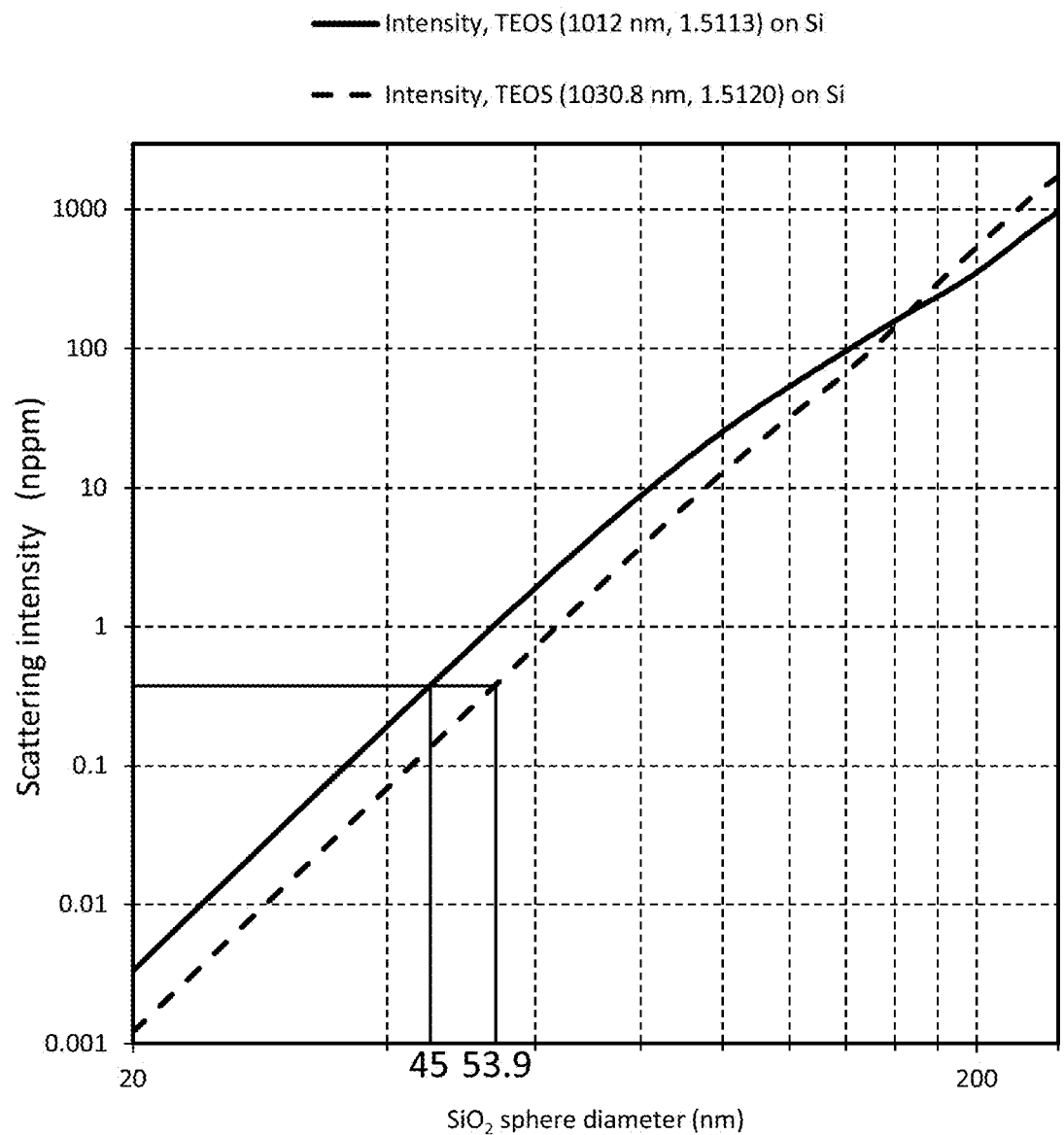
FIG. 3 is a graph of silicon dioxide sphere diameter vs. scattering intensity for two separate areas of the example wafer having a film of varying thickness shown in FIG. 2.

FIG. 3 shows two film curves for silicon dioxide spheres. The first curve (solid line) is the response that is obtained in the first zone 204 and the second curve (long-short dashed line), is the response that is obtained in the second zone 206, plotted against the scattering intensity on the Y axis. For this example, it is assumed that the film curve was determined from sphere depositions on a film wafer with very nearly the same thickness and refractive index that is obtained in zone 204. Thus, a 45 nm defect in zone 204, scattering approximately 0.4 nppm, will be correctly assigned a size of 45 nm. In contrast, the film thickness and refractive index in zone 206 diminishes light scattering intensity. FIG. 2 shows that a defect in zone 206 must have 53.9 nm size to scatter the same 0.4 nppm intensity. Thus, the film curve based on the response in zone 204 will incorrectly assign a 45 nm size to a 53.9 nm defect in zone 206, which is approximately 20% too small. A practical consequence of this sizing error would occur if the inspection recipe threshold was set to 45 nm: zone 206, encompassing an approximately 10 mm wide band at the wafer's edge, might be contaminated by a large plurality of defects between 45 and 53.9 nm, but these defects would be ignored because of the too small sizing error.

Figure 4:
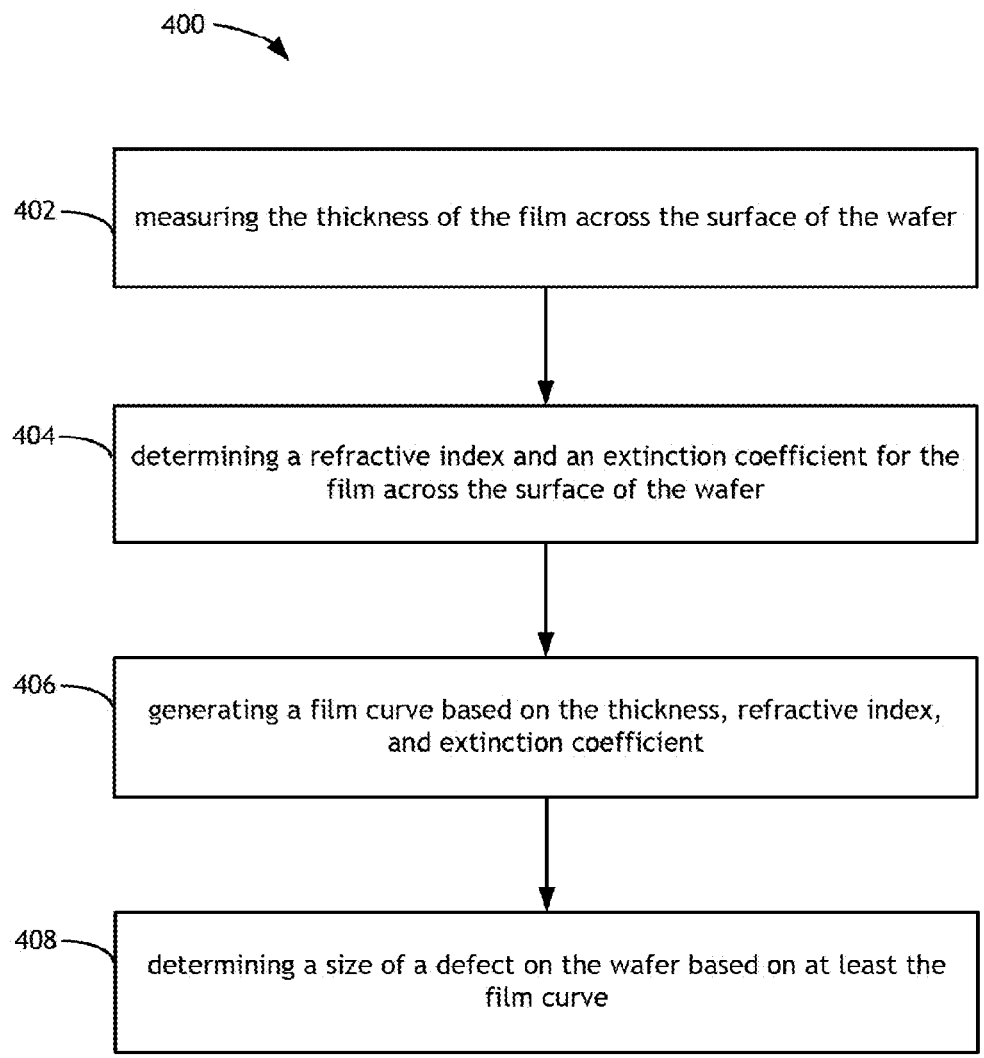
FIG. 4 is a flow diagram of a method for inspecting a wafer having a film deposited on a surface of the wafer.

The methods and systems of the present disclosure may help to improve the accuracy of defect sizing by accounting for the variation in film thickness across the surface of the wafer. One such method is shown in FIG. 4. The method 400 of FIG. 4 is may be used to inspect a wafer having a film deposited on a surface of the wafer. The thickness of the film may vary over the surface of the wafer. The method 400 includes the step of measuring the thickness of the film across the surface of the wafer 402. The method 400 also includes the step of determining a refractive index and an extinction coefficient for the film across the surface of the wafer 404. The next step of the method 400 is to generate a film curve based on the thickness, refractive index, and extinction coefficient 406. The method 400 also includes determining a size of a defect on the surface based on at least the film curve 408.

The step of measuring the thickness of the film across the surface of the wafer 402 of the method 400 may include measuring the film thickness using multi-wavelength surface scanning techniques in one embodiment. For example, determining the thickness of the film may include scanning the wafer with a plurality of light beams to generate a plurality of reflected light signals. The intensity of the plurality of reflected light signals may then be measured. The measured intensity may then be correlated to a film thickness, for example using a parametric curve that associates thickness for the film layer with optical parameter values for the reflected light beams.

The step of measuring the thickness of the film across the surface of the wafer 402 of the method 400 may also include measuring the film thickness using ellipsometry techniques. For example, the step 402 may include the step of measuring the polarization of a reflected light signal scanned on the surface of the wafer. Using the polarization values of the reflected light signals, it may be possible to determine the film thickness using ellipsometry techniques.

The method 400 shown in FIG. 4 also includes the step of determining a refractive index and an extinction coefficient for the film across the surface of the wafer 404. This step may be completed simultaneously with the step of measuring the thickness of the film across the surface of the wafer 402, or may be completed as a separate step. In one example, the step of determining the refractive index and the extinction coefficient for the film across the surface of the wafer 404 may include measuring the polarization of a reflected light signal scanned on the surface of the wafer. Based on this information, the refractive index and extinction coefficient may be determined using ellipsometry techniques.

The method 400 shown in FIG. 4 may be used on an unpatterned wafer. The method 400 may also be performed in real time. For example, when performing the method in real time, the film thickness, refractive index, and extinction coefficient values may be determined and a film curve may be created at the same time to size any defects found in that same location.

In one embodiment, the film thickness, refractive index, and extinction coefficient values vary over the surface of the wafer. The variance in the film thickness, refractive index, and extinction coefficient values at different locations may impact defect sizing if the correct values for the area of the wafer where the defect is located are not used. At the end of the scan, the wafer map shows the location and size of all defects. The defect sizes for the defects may be more accurate if the correct film thickness, refractive index, and extinction coefficient values are used to create the film curve based on the location of the defect.

Figure 5:
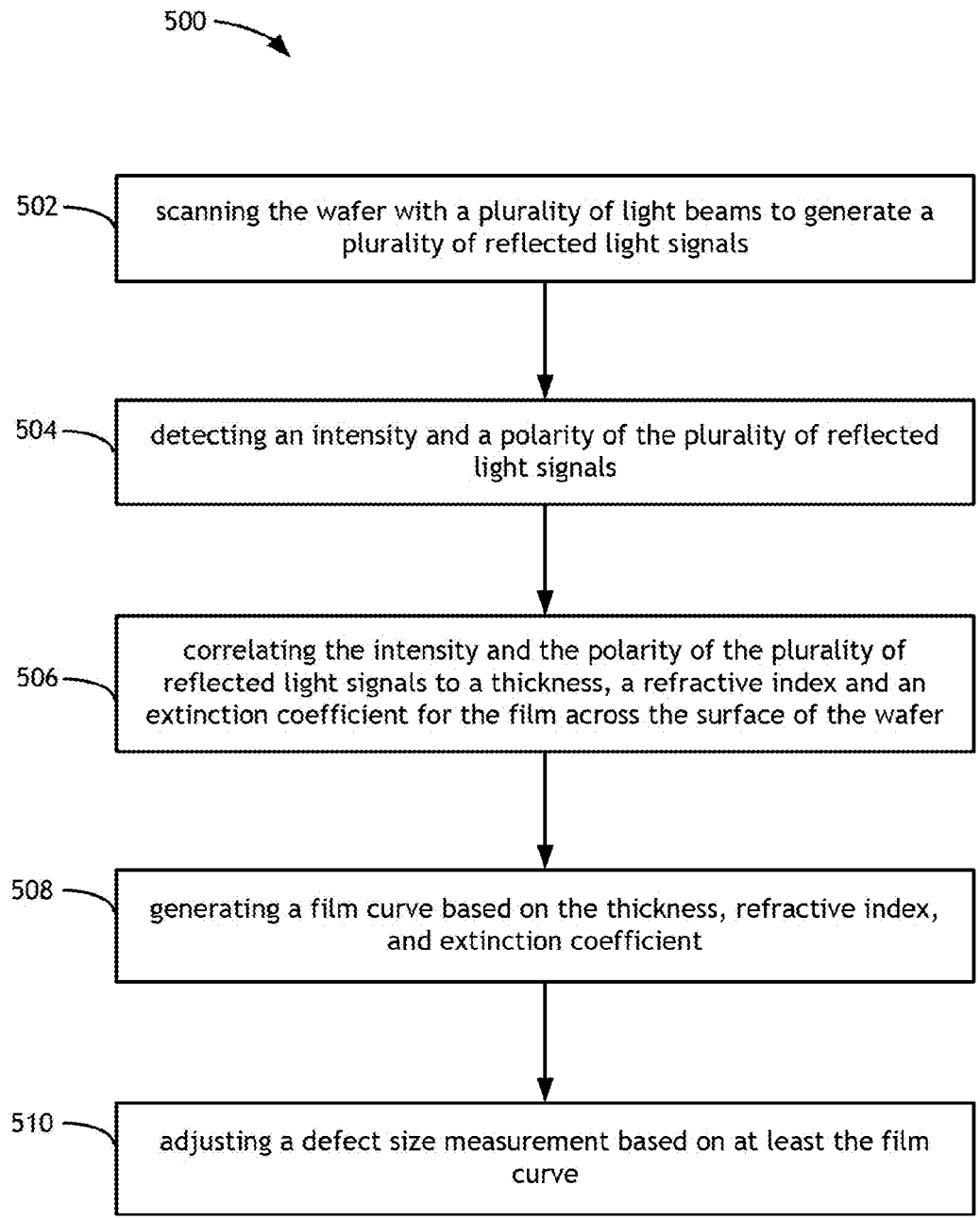
FIG. 5 is a flow diagram of a method for inspecting a wafer having a film deposited on a surface of the wafer.

The present disclosure is also directed to a method 500 shown in FIG. 5. The method 500 can be used for inspecting a wafer. The wafer includes a film deposited on a surface of the wafer. The film may have a variable thickness over the surface of the wafer. The method 500 includes the step of scanning the wafer with a plurality of light beams to generate a plurality of reflected light signals 502. The next step of the method 500 includes detecting an intensity and a polarity of the plurality of reflected light signals 504. This intensity and polarity can then be correlated to a thickness, a refractive index and an extinction coefficient for the film across the surface of the wafer in a further step 506 of the method 500. The method 500 also includes the step of generating a film curve based on the thickness, refractive index, and extinction coefficient 508. The method 500 also includes the step of adjusting a defect size measurement based on at least the film curve.

The step of correlating the intensity and the polarity of the plurality of reflected light signals to a thickness, a refractive index and an extinction coefficient for the film across the surface of the wafer 506 of the method 500 may be performed using ellipsometry techniques in one embodiment.

The step of adjusting a defect size measurement based on at least the film curve 510 of the method 500 may involve taking into account additional factors in adjusting the defect size measurement.

The method 500 shown in FIG. 5 may be used on an unpatterned wafer. The method 500 may also be performed in real time.

The step of generating a film curve based on the thickness, refractive index, and extinction coefficient 508 of the method 500 may be performed simultaneously, or nearly simultaneously with the step of correlating the intensity and polarity to a thickness, a refractive index and an extinction coefficient for the film across the surface of the wafer 506.

The methods and systems of the present disclosure may be implemented by modifying an existing inspection tool to incorporate the principles of the present disclosure. For example, an existing inspection system may already be configured to measure certain characteristics of a wafer, such as the intensity of reflected light. It may be possible to modify the existing inspection system to collect additional information in order to implement the principles of the present disclosure. This may include configuring the existing system to detect the polarity of reflected light in one example, so that ellipsometry techniques may be employed to determine film thickness, the extinction coefficient, and the refractive index. In one embodiment, an existing system may be modified to collect data on the polarity of reflected light. Similarly, the processing circuitry and/or processor of the existing system may be modified to incorporate a polarization module in one example.

Using the method 400 shown in FIG. 4 and the method 500 shown in FIG. 5, it may be possible to provide more accurate sizing of wafer defects over existing methods. It may be possible to create a film curve for the wafer without having to deposit polystyrene latex spheres of various known sizes onto the film. In addition, the methods may be performed in real time, which may provide accurate feedback on the characteristics of the wafer faster than existing methods.

It should be recognized that the various steps described throughout the present disclosure may be carried out by a single computing system or, alternatively, a multiple computing system. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

All of the methods described herein may include storing results of one or more steps of the method embodiments in a storage medium. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

It is further contemplated that each of the embodiments of the method described above may include any other step(s) of any other method(s) described herein. In addition, each of the embodiments of the method described above may be performed by any of the systems described herein.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed is:

1. A method for inspecting a wafer, the wafer including a film deposited on a surface of the wafer, the film having a thickness that varies over the surface of the wafer; the method comprising:

measuring the thickness of the film across the surface of the wafer;

determining a refractive index and an extinction coefficient for the film across the surface of the wafer by measuring the polarization of a reflected light signal scanned on the surface of the wafer;

generating a film curve based on the thickness, refractive index, and extinction coefficient, the film curve changes based on variances in the film thickness, refractive index, and extinction coefficient location on the wafer; and determining a size of a defect on the surface based on at least the film curve.

2. The method of claim 1, wherein the measuring the thickness of the film across the surface of the wafer includes:
scanning the wafer with a plurality of light beams to generate a plurality of reflected light signals;
detecting an intensity of the plurality of reflected light signals;
correlating the intensity of the plurality of reflected light signals to a thickness of the film.

3. The method of claim 1, wherein the method is performed in real time.

4. The method of claim 1, wherein the measuring the thickness of the film across the surface of the wafer includes measuring the polarization of a reflected light signal scanned on the surface of the wafer and using ellipsometry techniques to determine the thickness.

5. The method of claim 1, wherein the determining a refractive index and an extinction coefficient for the film across the surface of the wafer includes measuring the polarization of a reflected light signal scanned on the surface of the wafer and using ellipsometry techniques to determine the refractive index and extinction coefficient.

6. The method of claim 1, wherein the generating the film curve based on the thickness, refractive index, and extinction coefficient occurs at the same time as determining the refractive index and the extinction coefficient for the film across the surface of the wafer.

7. The method of claim 1, wherein the wafer is an unpatterned wafer.

8. A system for inspecting a wafer, the wafer including a film deposited on a surface of the wafer, the film having a thickness that varies over the surface of the wafer; the system comprising:
a plurality of light sources, the plurality of light sources arranged to project light towards the wafer;
a plurality of detectors, each detector of the plurality of detectors configured to measure light reflected from the wafer, each detector of the plurality of detectors also configured to measure the polarization of light reflected from the wafer;
a processor, the processor communicatively coupled to the plurality of detectors, the processor configured for calculating a refractive index, an extinction coefficient, and a film thickness for the film across the surface of the wafer, the processor further configured for generating a film curve based on the thickness, refractive index, and extinction coefficient of the wafer.

9. The system of claim 8, wherein the processor is configured for calculating a refractive index, an extinction coefficient, and a film thickness for the film across the surface of the wafer using ellipsometry.

10. The system of claim 8, wherein the processor is further configured for adjusting a defect size measurement based on the film curve.

11. The system of claim 8, wherein the processor is further configured to generate the film curve while calculating the refractive index, extinction coefficient, and film thickness for the film across the surface of the wafer.

12. The system of claim 8, wherein the wafer is an unpatterned wafer.

13. The system of claim 8, wherein the processor is further configured for calculating the refractive index, the extinction coefficient, and the film thickness for the film across the surface of the wafer and generating the film curve based on the thickness, refractive index, and extinction coefficient of the wafer in real time.

14. The system of claim 8, wherein the film curve changes based on variances in the film thickness, refractive index, and extinction coefficient location on the wafer.

15. A method for inspecting a wafer, the wafer including a film deposited on a surface of the wafer, the film having a thickness that varies over the surface of the wafer; the method comprising:
scanning the wafer with a plurality of light beams to generate a plurality of reflected light signals;
detecting an intensity and a polarity of the plurality of reflected light signals;
correlating the intensity and the polarity of the plurality of reflected light signals to a thickness, a refractive index and an extinction coefficient for the film across the surface of the wafer;
generating a film curve based on the thickness, refractive index, and extinction coefficient;
adjusting a defect size measurement based on at least the film curve.

16. The method of claim 15, wherein the method is performed in real time.

17. The method of claim 15, wherein the correlating the intensity and the polarity of the plurality of reflected light signals to a thickness, a refractive index and an extinction coefficient for the film across the surface of the wafer is performed using ellipsometry techniques.

18. The method of claim 15, wherein the wafer is an unpatterned wafer.

* * * * *